US010246754B1

(12) United States Patent
Meda et al.

(10) Patent No.: US 10,246,754 B1
(45) Date of Patent: Apr. 2, 2019

(54) MOLECULAR MARKERS LINKED TO DISEASE RESISTANCE IN SOYBEAN

(71) Applicant: Syngenta Participations AG, Basel (CH)

(72) Inventors: Anderson Rotter Meda, Londrina (BR); Becky Welsh Breitinger, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 26 days.

(21) Appl. No.: 15/378,394

(22) Filed: Dec. 14, 2016

Related U.S. Application Data

(63) Continuation of application No. 14/695,319, filed on Apr. 24, 2015.

(60) Provisional application No. 61/984,222, filed on Apr. 25, 2014.

(51) Int. Cl.
| | | |
|---|---|---|
| *A01H 5/10* | (2018.01) | |
| *C12Q 1/6895* | (2018.01) | |
| *A01H 1/02* | (2006.01) | |
| *A01H 1/04* | (2006.01) | |

(52) U.S. Cl.
CPC ............. *C12Q 1/6895* (2013.01); *A01H 1/02* (2013.01); *A01H 1/04* (2013.01); *A01H 5/10* (2013.01); *C12Q 2600/13* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| 4,458,066 | A | 7/1984 | Caruthers et al. |
| 8,669,414 | B2 | 3/2014 | Baley et al. |
| 9,091,681 | B2 | 7/2015 | Baley et al. |
| 2006/0137039 | A1 | 6/2006 | Sebastian |
| 2006/0288444 | A1 | 12/2006 | McCarroll |
| 2007/0006351 | A1 | 1/2007 | Terisky et al. |
| 2011/0185448 | A1 | 7/2011 | Yu et al. |
| 2015/0135359 | A1 | 5/2015 | Baley et al. |

FOREIGN PATENT DOCUMENTS

| WO | 2008/054546 | 5/2008 |
| WO | 2009/079729 | 7/2009 |
| WO | 2010/009404 | 1/2010 |
| WO | 2010/096227 | 8/2010 |

OTHER PUBLICATIONS

Meyer et al., 2009, Plant Physiology 150: 295-307.*
GS_Ba081117.R GS_Ba, Glycine syndetika genomic 3', genomic survey sequence, GenBank Accession No. HN804559, version HN804559.1, published Oct. 25, 2010.*
Glycine max polynucleotide encoding Rpp4 candidate 3, with a GenBank Accession No. FJ225395, version FJ225395.1, published Jul. 24, 2016.*
Anderson et al., "Development of simple sequence repeat markers for the soybean rust funus, Phakopsora pachyrhizi," Molecular Ecology Resources. (2008). vol. 8: 1310-1312.
Bromfield, K.R. and Hartwig, E.E., "Resistance to soybean rust and mode of inheritance," Crop Science. (1980) vol. 20(2): 254-255.
Calvo et al., "Two major recessive soybean genese conferring soybean rust resistance," Crop Science (2008), 28(4): 1350-1354.
Garcia et al., "Molecular mappnig of soybean rust (*Phakopsora pachyrhizi*) resistance genes: discovery of a novel locus and alleles," Theoretical and Applied Genetics (2008). vol. 117: 545-553.
Hartman et al., "Breeding for Resistance to Soybean Rust," (2005), Plant Disease, 89(6):664-666.
Hartwig and Bromfield, "Relationships among three genes conferring specific resistance to rust in soybeans," (1983). Crop Science, vol. 23: 237-239.
Hartwig, E.E., "Identification of a fourth major gene conferring resistance to soybean rust," (1983). Crop Science, vol. 23: 237-239.
Hyten et al., "Map Location of the Rpp1 Locus that confers resistance to soybean rust in soybean," (2007), Crop Science. 47(2): 837-840.
Hyten et al., "High-throughput genotyping with the GoldeGate assay in the complex genome of soybean," (2008). Theoretical and Applied Genetics vol. 116: 945-982.
McLean, R.J.and Bythe, D. "Inheritance of resistance to rust (*Phakopsora pachyrhizi*) in soybean," (1980). Aust. J. Ahric. Res. vol. 31: 951-956.
Miles et al.,"Evaluation of Soybean Germplasm for Resistance to Phakospora pachyrhizi," Plant Health Progress. Accessed on Feb. 15, 2013, 25 pages.
Monteros et al., "Mapping and Confirmation of the 'Hyuuga' Red-Brown Lesion Resistance Gene for Asian Soybean Rust," (2007). Crop Science. Vo. 47: 829-836.
Notification Concerning Transmittal of International Preliminary Report on Patentability (Chapter 1 of the Patent Cooperation Treaty) corresponding to International Patent Application No. PCT/US2010/021523 dated Sep. 1, 2011.

(Continued)

*Primary Examiner* — Bratislav Stankovic
(74) *Attorney, Agent, or Firm* — R. Kody Jones

(57) ABSTRACT

The present invention relates to methods and compositions for identifying, selecting and/or producing a soybean plant or germplasm having a Rpp4 resistance allele and resistance to *Phakosora pachyrhizi*. A soybean plant, part thereof and/or germplasm that has been identified, selected and/or produced by any of the methods of the present invention is also provided. Also provided are single nucleotide polymorphisms (SNPs) associated with resistance to pathogens; and compositions including amplification primer pairs capable of initiating DNA polymerization by a DNA polymerase on soybean nucleic acid templates to generate soybean marker amplicons.

1 Claim, No Drawings
Specification includes a Sequence Listing.

(56) References Cited

OTHER PUBLICATIONS

Notification of Transmittal of the International Search Report and the Written Opinion of the International Searching Authority, or the Declaration corresponding to International Patent Application No. PCT/US2009/051003 dated Feb. 5, 2010; and International Preliminary Report on Patentability dated Apr. 29, 2011.

Notification of Transmittal of the International Search Report and the Written Opinion of the International Searching Authority, or the Declaration corresponding to International Patent Application No. PCT/US2010/021523 dated Mar. 30, 2010.

Official Action corresponding to U.S. Appl. No. 13/054,760 dated Apr. 23, 2013.

Official Action corresponding to U.S. Appl. No. 13/054,760 dated Oct. 24, 2012.

Ray et al., "Genetics and mapping of adult plant rust resistance in soybean PI 587886 and PI 587880A," (2009). Theoretical and Applied Genetics, vol. 119 pp. 271-280.

Ribeiro et al., "Genetic control of Asian rust in soybean," (2007). Euphytica, vol. 157, pp. 15-25.

Silva et al., "Molecular mapping of two loci that confer resistance to Asian rust in soybean," (2008). Theoretical and Applied Genetics. vol. 117, pp. 57-63.

Zhu et al., "Single-nucleotide polymorphisms in soybean," (2003). Genetics, vol. 163, pp. 1123-1134.

Choi et al., Genetics, 2007 176:685-696, Supplemental Data File (58 additional pages disclosing consensus soybean genetic map).

Hyten, D.L. "Mappying soybean rust single gene resistance," Proc. 2007 Natl. Soybean Rust Symp, Louisville, KY (Dec. 12-14, 2007).

Lemos et al., Characterization of genes Rpp2, Rpp4, and Rpp5 for resistance to soybean rust, Euphytica, 2011, 182:53-64.

Meyer et al., Identification and analyses of candidate genes for Rpp4-mediated resistance to Asian soybean rust in soybean, Plant Physiology, May 2009, 150:295-307.

Maniatis et al., Molecular Cloning: A laboratory manual, Col Spring Harbor Laboratory, 1982; p. 324-343 and p. 387-389.

Gycine max clone GM_WBb0070A12, published May 5, 2009.

Glycine max clone GM_WBb176101 Rpp4 candidate 2 gene, published May 5, 2009.

Batley and Edwards, 2007, In: Association Mapping in Plants, pp. 95-102.

* cited by examiner

SEQUENCE LISTING

```
<160> NUMBER OF SEQ ID NOS: 66

<210> SEQ ID NO 1
<211> LENGTH: 157
<212> TYPE: DNA
<213> ORGANISM: Glycine max
<220> FEATURE:
<221> NAME/KEY: misc_feature
<222> LOCATION: (1)..(1)
<223> OTHER INFORMATION: r is a or g
<220> FEATURE:
<221> NAME/KEY: misc_feature
<222> LOCATION: (14)..(14)
<223> OTHER INFORMATION: y is c or t
<220> FEATURE:
<221> NAME/KEY: misc_feature
<222> LOCATION: (36)..(36)
<223> OTHER INFORMATION: k is t or g
<220> FEATURE:
<221> NAME/KEY: misc_feature
<222> LOCATION: (44)..(44)
<223> OTHER INFORMATION: y is c or t
<220> FEATURE:
<221> NAME/KEY: misc_feature
<222> LOCATION: (45)..(45)
<223> OTHER INFORMATION: w is t or a
<220> FEATURE:
<221> NAME/KEY: misc_feature
<222> LOCATION: (51)..(51)
<223> OTHER INFORMATION: r is a or g
<220> FEATURE:
<221> NAME/KEY: misc_feature
<222> LOCATION: (59)..(59)
<223> OTHER INFORMATION: y is c or t
<220> FEATURE:
<221> NAME/KEY: misc_feature
<222> LOCATION: (121)..(121)
<223> OTHER INFORMATION: w is t or a
<220> FEATURE:
<221> NAME/KEY: misc_feature
<222> LOCATION: (143)..(143)
<223> OTHER INFORMATION: s is g or c
<220> FEATURE:
<221> NAME/KEY: misc_feature
<222> LOCATION: (148)..(148)
<223> OTHER INFORMATION: y is c or t
<220> FEATURE:
<221> NAME/KEY: misc_feature
<222> LOCATION: (157)..(157)
<223> OTHER INFORMATION: w is t or a

<400> SEQUENCE: 1
rctgatagag gagytaaaag aatcaacttt gttggkggaa agtywctctc rtgaccgcyt      60
caacatgcat gacattgtgc gggatgttgc tctttcaata tcatccaaag aaaaacatgt     120
wttttttatg aaaaatggca tastagayga gtggccw                              157

<210> SEQ ID NO 2
<211> LENGTH: 468
<212> TYPE: DNA
```

```
<213> ORGANISM: Glycine max
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t

<400> SEQUENCE: 2
ttatctgttg attccaatan gataaaaaaa gaaaagttat cnggtgatca caagggatgc      60
aaaattcttc taacatccag aagnaaagaa gtaatatgta ataaaatgga tgtgcaggag     120
agatcaactt tctcggtagg agtccttgat gaaaacgagg caaagagttt ncttaagaaa     180
ttggcgggaa tacgtgccca aagttttgaa tttgatgaga aagtcattga aattgccaaa     240
atgtgcgatg gattgcctat ggcattagtt tccataggaa gggctctaaa gaataaaagc     300
tcctttgtat ggcaggatgt ctgtcaacna attaaangac aaagttttac anaagggcac     360
```
gaatctatng anttcnctgt aaanttgagn tntgancatc taaaaaatga gcagntgaaa    420 catatttnt tactgtgtgc tagaatggga aatgatgctt tgattatg    468

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
gctgatagag gagctaaaag aatcaact    28

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gaggccactc gtctactatg c    21

<210> SEQ ID NO 5
<211> LENGTH: 14
<212> TYPE: DNA
<213> ORGANISM: Artificial Sequence
<220> FEATURE:
<223> OTHER INFORMATION: Probe

<400> SEQUENCE: 5
catgaccgcc tcaa    14

<210> SEQ ID NO 6
<211> LENGTH: 15
<212> TYPE: DNA
<213> ORGANISM: Artificial Sequence
<220> FEATURE:
<223> OTHER INFORMATION: Probe

<400> SEQUENCE: 6
catgaccgct tcaac    15

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
tcgcattcga aagaggttaa agaaa    25

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gctcccattg tcatcctcac tac    23

<210> SEQ ID NO 9

```
<211> LENGTH: 15
<212> TYPE: DNA
<213> ORGANISM: Artificial Sequence
<220> FEATURE:
<223> OTHER INFORMATION: Probe

<400> SEQUENCE: 9
tctctgggac ggatt                                                    15

<210> SEQ ID NO 10
<211> LENGTH: 16
<212> TYPE: DNA
<213> ORGANISM: Artificial Sequence
<220> FEATURE:
<223> OTHER INFORMATION: Probe

<400> SEQUENCE: 10
tgatctctgg gatgga                                                   16

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
caaggactcc taccgagaaa gttg                                          24

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
gatcacaagg gatgcaaaat tcttc                                         25

<210> SEQ ID NO 13
<211> LENGTH: 21
<212> TYPE: DNA
<213> ORGANISM: Artificial Sequence
<220> FEATURE:
<223> OTHER INFORMATION: Probe

<400> SEQUENCE: 13
tacatattac ttctttactt c                                             21

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
acatattact tcttttcttc                                               20

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
```
ctcggtagga gtccttgatg aa                                              22

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
tgacagacat cctgccatac a                                               21

<210> SEQ ID NO 17
<211> LENGTH: 17
<212> TYPE: DNA
<213> ORGANISM: Artificial Sequence
<220> FEATURE:
<223> OTHER INFORMATION: Probe

<400> SEQUENCE: 17
aacgaggcaa agacttt                                                    17

<210> SEQ ID NO 18
<211> LENGTH: 17
<212> TYPE: DNA
<213> ORGANISM: Artificial Sequence
<220> FEATURE:
<223> OTHER INFORMATION: Probe

<400> SEQUENCE: 18
aacgaggcaa agtgttt                                                    17

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gagcaacatc ccgcacaatg                                                 20

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
ccacacaatt agagaagcga gaaac                                           25

<210> SEQ ID NO 21
<211> LENGTH: 15
<212> TYPE: DNA
<213> ORGANISM: Artificial Sequence
<220> FEATURE:
<223> OTHER INFORMATION: Probe

<400> SEQUENCE: 21
tgcatgttga agcgg                                                      15

<210> SEQ ID NO 22
<211> LENGTH: 15
<212> TYPE: DNA

<213> ORGANISM: Artificial Sequence
<220> FEATURE:
<223> OTHER INFORMATION: Probe

<400> SEQUENCE: 22
catgttgagg cggtc                                                    15

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ggatgtgcag gagagatcaa c                                             21

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gcacgtattc ccgccaattt c                                             21

<210> SEQ ID NO 25
<211> LENGTH: 16
<212> TYPE: DNA
<213> ORGANISM: Artificial Sequence
<220> FEATURE:
<223> OTHER INFORMATION: Probe

<400> SEQUENCE: 25
ctcggtagga gtcctt                                                   16

<210> SEQ ID NO 26
<211> LENGTH: 17
<212> TYPE: DNA
<213> ORGANISM: Artificial Sequence
<220> FEATURE:
<223> OTHER INFORMATION: Probe

<400> SEQUENCE: 26
ctcggtagga gttcttg                                                  17

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ggatgtgcag gagagatcaa c                                             21

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
gcacgtattc ccgccaattt c                                             21

<210> SEQ ID NO 29
<211> LENGTH: 18
<212> TYPE: DNA
<213> ORGANISM: Artificial Sequence
<220> FEATURE:
<223> OTHER INFORMATION: Probe

<400> SEQUENCE: 29
taggagtcct tgaagaaa                                                 18

<210> SEQ ID NO 30
<211> LENGTH: 18
<212> TYPE: DNA
<213> ORGANISM: Artificial Sequence
<220> FEATURE:
<223> OTHER INFORMATION: Probe

<400> SEQUENCE: 30
taggagtcct tgatgaaa                                                 18

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ggatgtgcag gagagatcaa ct                                            22

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
gcacgtattc ccgccaattt c                                             21

<210> SEQ ID NO 33
<211> LENGTH: 18
<212> TYPE: DNA
<213> ORGANISM: Artificial Sequence
<220> FEATURE:
<223> OTHER INFORMATION: Probe

<400> SEQUENCE: 33
agtccttgat gaaaacga                                                 18

<210> SEQ ID NO 34
<211> LENGTH: 20
<212> TYPE: DNA
<213> ORGANISM: Artificial Sequence
<220> FEATURE:
<223> OTHER INFORMATION: Probe

<400> SEQUENCE: 34
agtccttgat gaaaatgagg                                               20

<210> SEQ ID NO 35
<211> LENGTH: 20
<212> TYPE: DNA
<213> ORGANISM: Artificial Sequence
<220> FEATURE:

```
<223> OTHER INFORMATION: Primer

<400> SEQUENCE: 35
agtccttgat gaaaatgagg                                          20

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
ttctcggtag gagtccttga tg                                       22

<210> SEQ ID NO 37
<211> LENGTH: 15
<212> TYPE: DNA
<213> ORGANISM: Artificial Sequence
<220> FEATURE:
<223> OTHER INFORMATION: Probe

<400> SEQUENCE: 37
aaggaaactc tgcgc                                               15

<210> SEQ ID NO 38
<211> LENGTH: 16
<212> TYPE: DNA
<213> ORGANISM: Artificial Sequence
<220> FEATURE:
<223> OTHER INFORMATION: Probe

<400> SEQUENCE: 38
aaggaaactc tttgcc                                              16

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
ctcggtagga gtccttgatg a                                        21

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
ggcacgtatt cccgccaat                                           19

<210> SEQ ID NO 41
<211> LENGTH: 17
<212> TYPE: DNA
<213> ORGANISM: Artificial Sequence
<220> FEATURE:
<223> OTHER INFORMATION: Probe

<400> SEQUENCE: 41
aggcaaagag tttcctt                                             17
```

```
<210> SEQ ID NO 42
<211> LENGTH: 16
<212> TYPE: DNA
<213> ORGANISM: Artificial Sequence
<220> FEATURE:
<223> OTHER INFORMATION: Probe

<400> SEQUENCE: 42
aggcaaagag tttgct                                                      16

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
gcacattttg gcaatttcaa tgac                                             24

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ggatgtgcag gagagatcaa c                                                21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
tcaaattcaa aactttggac a                                                21

<210> SEQ ID NO 46
<211> LENGTH: 20
<212> TYPE: DNA
<213> ORGANISM: Artificial Sequence
<220> FEATURE:
<223> OTHER INFORMATION: Probe

<400> SEQUENCE: 46
caaattcaaa actttgggca                                                  20

<210> SEQ ID NO 47
<211> LENGTH: 20
<212> TYPE: DNA
<213> ORGANISM: Artificial Sequence
<220> FEATURE:
<223> OTHER INFORMATION: Probe

<400> SEQUENCE: 47
aggcaatcca tcgcacattt                                                  20

<210> SEQ ID NO 48
<211> LENGTH: 21
<212> TYPE: DNA
<213> ORGANISM: Artificial Sequence
<220> FEATURE:
<223> OTHER INFORMATION: Primer
```

```
<400> SEQUENCE: 48
tttctcggta ggagtccttg a                                              21

<210> SEQ ID NO 49
<211> LENGTH: 18
<212> TYPE: DNA
<213> ORGANISM: Artificial Sequence
<220> FEATURE:
<223> OTHER INFORMATION: Probe

<400> SEQUENCE: 49
ctttctcatc aaagtcaa                                                  18

<210> SEQ ID NO 50
<211> LENGTH: 19
<212> TYPE: DNA
<213> ORGANISM: Artificial Sequence
<220> FEATURE:
<223> OTHER INFORMATION: Probe

<400> SEQUENCE: 50
ctttctcatc aaattcaaa                                                 19

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
gcccttccta tggaaactaa tgc                                            23

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ttctcggtag gagtccttga tg                                             22

<210> SEQ ID NO 53
<211> LENGTH: 19
<212> TYPE: DNA
<213> ORGANISM: Artificial Sequence
<220> FEATURE:
<223> OTHER INFORMATION: Probe

<400> SEQUENCE: 53
ttggcaattt caataactt                                                 19

<210> SEQ ID NO 54
<211> LENGTH: 17
<212> TYPE: DNA
<213> ORGANISM: Artificial Sequence
<220> FEATURE:
<223> OTHER INFORMATION: Probe

<400> SEQUENCE: 54
tggcaatttc aatgact                                                   17

<210> SEQ ID NO 55
<211> LENGTH: 23
```

```
<212> TYPE: DNA
<213> ORGANISM: Artificial Sequence
<220> FEATURE:
<223> OTHER INFORMATION: Primer

<400> SEQUENCE: 55
gcccttccta tggaaactaa tgc                                          23

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
ctcggtagga gtccttgatg a                                            21

<210> SEQ ID NO 57
<211> LENGTH: 16
<212> TYPE: DNA
<213> ORGANISM: Artificial Sequence
<220> FEATURE:
<223> OTHER INFORMATION: Probe

<400> SEQUENCE: 57
aggcaatcca tcacac                                                  16

<210> SEQ ID NO 58
<211> LENGTH: 17
<212> TYPE: DNA
<213> ORGANISM: Artificial Sequence
<220> FEATURE:
<223> OTHER INFORMATION: Probe

<400> SEQUENCE: 58
ataggcaatc catcgca                                                 17

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
tgccaaaatg tgcgatggat tg                                           22

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
tgacagacat cctgccatac a                                            21

<210> SEQ ID NO 61
<211> LENGTH: 17
<212> TYPE: DNA
<213> ORGANISM: Artificial Sequence
<220> FEATURE:
<223> OTHER INFORMATION: Probe

<400> SEQUENCE: 61
```

-continued

```
ccataggaag ggcacta                                                    17

<210> SEQ ID NO 62
<211> LENGTH: 17
<212> TYPE: DNA
<213> ORGANISM: Artificial Sequence
<220> FEATURE:
<223> OTHER INFORMATION: Probe

<400> SEQUENCE: 62
ccataggaag ggctcta                                                    17

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
ttctcggtag gagtccttga tg                                              22

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
gcccttccta tggaaactaa tgc                                             23

<210> SEQ ID NO 65
<211> LENGTH: 17
<212> TYPE: DNA
<213> ORGANISM: Artificial Sequence
<220> FEATURE:
<223> OTHER INFORMATION: Probe

<400> SEQUENCE: 65
tccttaagaa agaggcg                                                    17

<210> SEQ ID NO 66
<211> LENGTH: 16
<212> TYPE: DNA
<213> ORGANISM: Artificial Sequence
<220> FEATURE:
<223> OTHER INFORMATION: Probe

<400> SEQUENCE: 66
taagaaattg gcggga                                                     16
```

MOLECULAR MARKERS LINKED TO DISEASE RESISTANCE IN SOYBEAN

RELATED APPLICATION INFORMATION

This application is a continuation of U.S. patent application Ser. No. 14/695,319 filed on Apr. 24, 2015 which claims benefit of U.S. Provisional Patent Application No. 61/984,222, filed 25 Apr. 2014, the contents of each which are herein incorporated by reference.

STATEMENT REGARDING ELECTRONIC SUBMISSION OF A SEQUENCE LISTING

A Sequence Listing in ASCII text format, submitted under 37 C.F.R. § 1.821, entitled "80511-US-REG-ORG-NAT-1_Sequence_Listing_ST25.txt", 14.3 kb in size, generated on 25 Apr. 2014 and filed via EFS-Web is provided in lieu of a paper copy. This Sequence Listing is hereby incorporated by reference into the specification for its disclosures.

FIELD OF THE INVENTION

The presently disclosed subject matter relates to markers associated with pathogen resistance and methods of use therefor. More particularly, the presently disclosed subject matter relates to markers that are associated with a particular region of Glycine sp. chromosome 18 that is associated with resistance to Phakopsora pachyrhizi, and for producing soybean lines with improved resistance to Phakopsora pachyrhizi, the methods involving the use of markers developed from this region in a precision plant breeding program.

BACKGROUND

Soybeans are an important global source of protein and oil. Soy protein serves primarily as an animal feed containing all of the essential amino acids. In 2011, soybeans represented 56 percent of the worldwide oil seed production. Soybeans along with corn represent the two most important crops in the United States.

Soybean plants are vulnerable to a wide range of bacterial, fungal, viral, and parasitic diseases. A fungal disease called Asian Soy Rust or ASR has been rapidly spreading throughout the world. The fungus causing this disease is Phakopsora pachyrhizi. The disease is characterized by small tan-colored lesions to forming on the lower surface of the leaf. The lesions release spores into the wind. The wind carried spores have been reported to travel four hundred miles in a day. Originating in Asia, the disease spread to Africa in 1997, South America in 2001, and to the United States in 2004.

A timely response is needed to combat the threat of Asian Soybean Rust. Fungicide applications can prevent significant yield loss. Commercial germplasm in the U.S. and much of the world lacks resistance to Asian Soybean Rust, and the development of disease resistant cultivars provides another line of defense. There are currently five known dominant resistance genes in soybean known as Rpp1, 2, 3, 4, and 5.

SUMMARY OF THE INVENTION

Compositions and methods for identifying, selecting and producing soybean plants having Rpp4 resistance alleles are provided. Soybean plants and/or soybean germplasms and/or parts thereof having Rpp4 resistance alleles are also provided.

Accordingly, in one aspect of this invention, a method of identifying and/or selecting a soybean plant or germplasm having an Rpp4 resistance allele is provided, the method comprising: detecting, in a soybean plant or germplasm, the presence of a genetic marker associated with an Rpp4 resistance allele, wherein said genetic marker is a G at nucleotide 59 of SEQ ID NO:1 (SY3131); thereby identifying or selecting a soybean plant or germplasm having an Rpp4 resistance allele.

In other aspects, the present invention provides a method of producing a soybean plant having an Rpp4 resistance allele, the method comprising: (a) detecting, in a soybean germplasm, the presence of a genetic marker associated with an Rpp4 resistance allele, wherein said genetic marker comprises is a G at nucleotide 59 of SEQ ID NO:1 (SY3131); thereby identifying or selecting a soybean plant or germplasm having an Rpp4 resistance allele.

A further aspect of this invention provides a method of introgressing an Rpp4 resistance allele into a soybean germplasm that is lacking the Rpp4 resistance allele, the method comprising: (a) crossing a donor parental soybean line comprising a genetic marker associated with an Rpp4 resistance allele with a recurrent parental soybean line that lacks said marker to produce progeny; (b) selecting progeny comprising said marker and backcrossing said progeny with the recurrent parental soybean line, wherein said progeny are selected by detecting, in their genomes, the presence of said marker associated with an Rpp4 resistance allele, wherein said marker comprises: is a G at nucleotide 59 of SEQ ID NO:1 (SY3131); (c) backcrossing the selected progeny of (b) with the recurrent parental soybean line to produce further progeny; and (d) repeating steps (b) to (c) one or more times, thereby introgressing the Rpp4 resistance allele into the recurrent parental line, and thus introgressing the Rpp4 resistance allele into the soybean germplasm that is lacking the Rpp4 resistance allele.

In some embodiments an oligonucleotide has a sequence complementary to one allele of a known target polynucleotide which, optionally, has a known polymorphism, paramorphism, or mutation. In other embodiments an oligonucleotide may have a sequence complimentary to a sequence which distinguishes between members of gene families. In some embodiments the known target polynucleotide may distinguish Rpp4C4 in PI45902513 from Rpp4C1-C3 in an ASR susceptible line such as Williams 82. In some embodiments known polymorphisms or paramorphisms, or mutations used to distinguish Rpp4C4 in PI459025B from Rpp4C1-C3 in an ASR susceptible line such as Williams 82 are SNP 1, 2, 6, 7, 9, 10 or 11. In some embodiments, the present invention is a method for selecting a soybean plant with Asian soybean rust resistance loci Rpp4 with a PCR assay, comprising a first primer which hybridizes to SNP 1. In other embodiments the first primer may hybridize to SNP 1 and/or SNP 2. In further embodiments the sequence of the first primer may be SEQ ID NO. 3. In other embodiments an oligonucleotide that has a sequence complementary to one allele of a known target polynucleotide which, optionally, has a known polymorphism, paramorphism, or mutation may be used as an allele-specific hybridization probe. In some embodiments of the invention, the polymorphism, paramorphism, or mutation recognized by the allele-specific hybridization probe may distinguish Rpp4C4 in PI45902513 from Rpp4C1-C3 in an ASR susceptible line such as Williams 82. In some embodiments the method for selecting a soybean plant with Asian soybean rust resistance loci Rpp4 utilizes a hybridization probe which recognizes SNP 6 and/or SNP7. In some embodiments the hybridization probe may be SEQ ID NO. 5. In some embodiments a second primer may distinguish Rpp4C4 in PI459025B from Rpp4C1-C3 in an ASR susceptible line such as Williams 82. In some embodiments a second primer may hybridize to SNP 9 and/or SNP 10 and/or SNP 11. In some embodiments the second primer may be SEQ ID NO. 4.

Compositions comprising a primer pair capable of amplifying a nucleic acid sample isolated from a maize plant or germplasm to generate a marker associated with an Rpp4 resistance allele are also provided. Such compositions may comprise, consist essentially of or consist of one of the amplification primer pairs and/or probes identified in Table 1.

These and other aspects of the invention are set forth in more detail in the description of the invention below.

DETAILED DESCRIPTION

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

Disclosed herein is the identification and design of genetic markers (SNPs and/or combinations of SNPs) that can be used to identify alleles associated with Asian Soybean Rust resistance in soybean.

Therefore, present invention provides compositions and methods for identifying, selecting and/or producing soybean plants having one or more Rpp4 resistance alleles. In addition, the present invention provides soybean plants and/or soybean germplasm having within their genomes one or more SNP markers associated with one or more Rpp4 resistance alleles. These SNPs are located on *Glycine* sp. Chromosome 18 (Linkage Group G).

Definitions

Unless defined otherwise, all technical and scientific terms used herein have the same meaning as commonly understood to one of ordinary skill in the art to which the presently disclosed subject matter belongs.

Following long-standing patent law convention, the articles "a", "an", and "the" refer to "one or more" when used in this application, including in the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates in some embodiments to SNPs, it is in some instances more accurate to refer to a "haplotype" (i.e., an allele of a chromosomal segment) instead of "allele". However, in such instances, the term "allele" should be understood to comprise the term "haplotype".

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

As used herein, the phrase "associated with" refers to a recognizable and/or assayable relationship between two entities. For example, a trait, locus, QTL, SNP, gene, marker, phenotype, etc. is "associated with pathogen resistance" if the presence or absence of the trait, locus, QTL, SNP, gene, marker, phenotype, etc., influences an extent or degree of pathogen resistance (e.g., resistance to Asian Soybean Rust). In some embodiments, an allele associated with pathogen resistance comprises an allele having a G at nucleotide 59 of SEQ ID NO: 1. In other embodiments, an allele associated with pathogen resistance comprises an allele having a C at nucleotide 1 of SEQ ID NO: 1, a G at nucleotide 14 of SEQ ID NO: 1, a T at nucleotide 51 of SEQ ID NO: 1, a G at nucleotide 59 of SEQ ID NO: 1, a C at nucleotide 143 of SEQ ID NO: 1, a G at nucleotide 148 of SEQ ID NO: 1, and an A at nucleotide 157 of SEQ ID NO: 1.

As used herein, the term "backcross", and grammatical variants thereof, refers to a process in which a breeder crosses a progeny individual back to one of its parents, for example, a first generation individual with one of the parental genotypes of the first generation individual. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence the linear array of genes.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to oligonucleotides that comprise specific sequences (e.g., any of SEQ ID NOs: 1-2) that can be employed for assaying the genomes of plants (e.g., soybeans) for the presence of SNPs. It is understood that the presently disclosed subject matter thus also encompasses oligonucleotides that in some embodiments consist essentially of specific sequences that can be employed for assaying the genomes of plants for the presence of SNPs, as well as oligonucleotides that in some embodiments consist of specific sequences (e.g., any of SEQ ID NOs: 3-66) that can be employed for assaying the genomes of plants for the presence of SNPs. Similarly, it is also understood that in some embodiments the methods of the presently disclosed subject matter comprise the steps that are disclosed herein, in some embodiments the methods of the presently disclosed subject matter consist essentially of the steps that are disclosed herein, and in some embodiments the methods of the presently disclosed subject matter consist of the steps that are disclosed herein.

As used herein, the terms "cultivar" and "variety" refer to a group of similar plants that by structural or genetic features and/or performance can be distinguished from other varieties within the same species.

Disclosed herein are exemplary polymorphisms that are associated with increases and decreases in plant resistance to various pathogens (e.g., Asian Soybean Rust). With respect to the instant disclosure, the phrase "favorable allele" refers in some embodiments to an allele that when present results in a quantitatively higher resistance to one or more pathogens versus the case when the "unfavorable allele" is present. It is noted, however, then in the case where a lower pathogen resistance is desirable, the alleles listed in the instant disclosure (e.g., in Tables 4) as "unfavorable" would in fact be the favorable alleles. As such, the terms "favorable" and "unfavorable" are employed in Tables 4 in the context of increased pathogen resistance, and would be reversed in the context of decreased pathogen resistance.

As used herein, the term "gene" refers to a hereditary unit including a sequence of DNA that occupies a specific location on a chromosome and that contains the genetic instruction for a particular characteristics or trait in an organism. A "gene family" is a set of several similar genes, formed by duplication of a single original gene, and generally with similar biochemical functions.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the phrase "informative fragment" refers to a nucleic acid molecule and/or its nucleotide sequence that allows for the proper identification of which allele of an allele set (e.g., an SNP) the nucleic acid molecule and/or the nucleotide sequence corresponds to. For example, whereas the locus that corresponds to SEQ ID NO: 1 comprises to an A or a G SNP at position 59 of SEQ ID NO: 1, an "informative fragment" of SEQ ID NO: 1 would be any sequence that comprises position 59 of SEQ ID NO: 1. Similarly, an informative fragment of the same locus that is isolated from a soybean genome that might differ to a degree from SEQ ID NO: 1 could include the nucleotide that corresponds to position 59 of SEQ ID NO: 1, thereby allowing the nucleotide that is present in that position of the differing soybean genome to be determined.

As used herein, the terms "introgression", "introgressed", and "introgressing" refer to both a natural and artificial process whereby genomic regions of one species, variety, or cultivar are moved into the genome of another species, variety, or cultivar, by crossing those species, varieties, or cultivars. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, in some embodiments two alleles on the same chromosome are said to be "linked" when they segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, two loci are linked if they are within 50, 25, 20, 15, 10, 5, 4, 3, 2, 1, 0.5, or 0.1 centiMorgans (cM) of each other. For example, in some embodiments an SNP is linked to a marker if it is within 50, 25, 20, 15, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species.

As used herein, the term "marker" refers to an identifiable position on a chromosome the inheritance of which can be monitored. In some embodiments, a marker comprises a known or detectable nucleic acid sequence.

In some embodiments, a marker corresponds to an amplification product generated by amplifying a *Glycine* sp. nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Glycine* sp. genomic DNA with a particular set of primers. In some embodiments, the amplifying is by PCR, and the primers are PCR primers that are designed to hybridize to opposite strands of the *Glycine* sp. genomic DNA in order to amplify a *Glycine* sp. genomic DNA sequence present between the sequences to which the PCR primers hybridize in the *Glycine* sp. genomic DNA. In some embodiments, a marker that "corresponds to" an amplified fragment is a marker that has the same sequence of one of the strands of the amplified fragment.

As used herein, the term "soybean" refers to a plant, or a part thereof, of the genus *Glycine* including, but not limited to *Glycine max*.

As used herein, the phrase "soybean-specific DNA sequence" refers to a polynucleotide sequence having a nucleotide sequence homology of in some embodiments more than 50%, in some embodiments more than 60%, in some embodiments more than 70%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the species *Glycine* that shows the greatest similarity to it. In the case of markers for any of the pathogen resistance loci disclosed herein, a "soybean-specific DNA sequence" can comprise a part of the DNA sequence of a soybean genome that flanks and/or is a part of any of the pathogen resistance loci disclosed herein.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A molecular marker "linked to" or "associated with" a pathogen resistance gene or locus as defined herein can thus refer to SNPs, insertion mutations, as well as more usual AFLP markers or any other type of marker used in the field.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 60, 70, 80, 90, 95, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein, the term "offspring" plant refers to any plant resulting as progeny from a vegetative or sexual reproduction from one or more parent plants or descendants thereof. For instance, an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

"Paralogs" are genes related by duplication within a genome. "Orthologs" retain the same function in the course of evolution, whereas paralogs evolve new functions, even if these are related to the original one. A "paramorphism" is a single nucleotide substitution between paralogs.

As used herein, the term "phenotype" refers to a detectable characteristic of a cell or organism, which characteristics are at least partially a manifestation of gene expression. An exemplary phenotype is a pathogen resistance phenotype. Pathogen resistance phenotypes includes, but is not limited to Asian Soybean Rust resistance.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" refers to a genetically heterogeneous collection of plants that in some embodiments share a common genetic derivation.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer.

In the context of amplification primers, these are typically provided as a pair of bi-directional primers consisting of one forward and one reverse primer or provided as a pair of forward primers as commonly used in the art of DNA amplification such as in PCR amplification.

As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions. SNP genotyping can be performed with real-time PCR assays as well as many PCR based SNP genotyping methods known in the art.

Continuing, the term "probe" refers to a single-stranded oligonucleotide sequence that will form a hydrogen-bonded duplex with a complementary sequence in a target nucleic acid sequence analyte or its cDNA derivative.

As used herein, the term "quantitative trait locus" (QTL; plural quantitative trait loci; QTLs) refers to a genetic locus (or loci) that controls to some degree a numerically representable trait that, in some embodiments, is continuously distributed. As such, the term QTL is used herein in its art-recognized meaning to refer to a chromosomal region containing alleles (e.g., in the form of genes or regulatory sequences) associated with the expression of a quantitative phenotypic trait. Thus, a QTL "associated with" pathogen resistance refers to one or more regions located in some embodiments on *Glycine* sp. chromosome 18 and/or in linkage group G that includes at least one gene the expression of which influences a level of resistance to one or more pathogens and/or at least one regulatory region that controls the expression of one or more genes involved in pathogen resistance. QTLs can be defined by indicating their genetic location in the genome of a specific *Glycine* sp. accession using one or more molecular genomic markers. One or more markers, in turn, indicate a specific locus. Distances between loci are usually measured by the frequency of crossovers between the loci on the same chromosome (e.g., chromosome 18). The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the end-point markers is indicative of the size of the QTL. As used herein, the term "regenerate", and grammatical variants thereof, refers in some embodiments to the production of a plant from tissue culture and use to the production of a plant by growing in soil.

As used herein, the term "resistant" and "resistance" encompass both partial and full resistance to infection with and/or damage by a pathogen (e.g., infection by a pathogen that causes Asia Soybean Rust). A susceptible plant can either be non-resistant or have lower levels of resistance relative to a resistant plant. The term is used to include such separately identifiable forms of resistance as "full resistance", "immunity", "hypersensitivity", "intermediate resistance", "partial resistance", "tolerance" and "susceptibility".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Exemplary guidelines for the hybridization of nucleic acids can be found in Tijssen (1993) *in Laboratory Techniques in Biochemistry and Molecular Biology*, Elsevier, New York, N.Y., United States of America; Ausubel et al. (1999) *Short Protocols in Molecular Biology* Wiley, New York, N.Y., United States of America; and Sambrook & Russell, 2001 (supra). Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). In some embodiments, hybridization conditions are employed (in some embodiments in conjunction with considerations of the nucleotide sequences of the polynucleotides that are intended to hybridize) such that oligonucleotides (such as, but not limited to the forward, reverse, and assay primers listed in Table 4) only hybridize to sequences with which they can form 100% matched duplexes (i.e., the oligonucleotide is 100% identical to the reverse-complement of the sequence to which it hybridizes or includes a 3' sequence that is 100% identical to the reverse-complement of the sequence to which it hybridizes allowing the oligonucleotide to function in an amplification reaction.)

As used herein, the term "susceptible" refers to a plant having no resistance to infection with and/or damage by a pathogen resulting in the plant being affected by the pathogen, in some embodiments resulting in disease symptoms. The term "susceptible" is therefore equivalent to "non-resistant". Alternatively, the term "susceptible" can be employed in a relative context, in which one plant is considered "susceptible" because it is less resistant to infection with and/or damage by a pathogen than is a second plant (which in the context of these terms in a relative usage, would be referred to as the "resistant" plant).

Genetic Mapping

Genetic loci correlating with particular phenotypes, such as resistance to Asian Soybean Rust, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with Rpp4 resistance alleles and thus, associated with resistance to particular races of Asian Soybean Rust. Detection of these markers and/or other linked markers can be used to identify, select and/or produce plants having Rpp4 resistance alleles, and thus, having resistance to Asian Soybean Rust and/or to eliminate plants from breeding programs or from planting that do not have a Rpp4 resistance allele and are not resistant to Asian Soybean Rust.

Markers Associated with an Rpp4 Resistance Allele

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) Methods in Plant Molecular Biology and Biotechnology, CRC Press, Boca Raton, Fla., United States of America; Zietkiewicz et al. (1994) Genomics 20:176-183.

The recombination frequencies of genetic markers on different chromosomes and/or in different linkage groups are generally 50%. Between genetic markers located on the same chromosome or in the same linkage group, the recombination frequency generally depends on the physical distance between the markers on a chromosome. A low recombination frequency typically corresponds to a low genetic distance between markers on a chromosome. Comparison of all recombination frequencies among a set of genetic markers results in the most logical order of the genetic markers on the chromosomes or in the linkage groups. This most logical order can be depicted in a linkage map. A group of adjacent or contiguous markers on the linkage map that is associated with an increased level of resistance to a disease (e.g., to a reduced incidence of acquiring the disease upon infectious contact with the disease agent and/or a reduced lesion growth rate upon establishment of infection) can provide the position of a locus associated with resistance to that disease. The present invention provides SNP markers and/or combination of SNP markers that can be used in various aspects of the presently disclosed subject matter as set forth herein.

Thus, the SNP markers provided herein can be used for detecting the presence of one or more Rpp4 resistance alleles in soybean plant or germplasm, and can therefore be used in methods involving marker-assisted breeding and selection of Asian Soybean Rust-resistant soybean plants/ soybean plants having one or more Rpp4 resistance alleles.

In some embodiments, methods for detecting the presence of an SNP in a soybean plant or germplasm can comprise providing a oligonucleotide or polynucleotide capable of hybridizing under stringent hybridization conditions to a nucleotide sequence of a SNP disclosed herein, contacting the oligonucleotide or polynucleotide with genomic nucleic acid (or a fragment thereof, including, but not limited to a restriction fragment thereof) of the soybean plant or germplasm, and determining the presence of the SNP by the specific hybridization of the oligonucleotide or polynucleotide to the soybean genomic nucleic acid (or the fragment thereof).

Accordingly, SNP markers associated with Rpp4 resistance alleles are identified herein. The SNP markers of the present invention are described herein with respect to their position in Chromosome 18 (linkage group G) of the soybean genome (e.g., *Glycine max* L. cultivar Williams 82) (reference sequence found at the Soybase database, soybase.org). Thus, Table 1 compares the markers of this invention with previously published markers showing the corresponding name, sequence identifier (SEQ ID NO. 1), the location of the SNP on Chromosome 18 of soybean cultivar Williams 82 (8× public build; SoyBase internet resource (soybase.org/SequenceIntro.php)).

TABLE 1

| Marker | AF162283 | SY313 1 (SEQ ID NO 1) | Satt 288 |
|---|---|---|---|
| Linkage Group | G | G | G |
| Genetic Position | 79.793 cM | 76.0 cM | 71.577 |
| Chromosome | Gm18 | Gm18 | Gm18 |
| Physical Position | 57.4M | 55.8M | 55.4 |

Meyer et al. Plant Phys 150, 295-307 in supplemental figure 4 show a ~1200 bp alignment of five Asian Soybean Rust Rpp4 resistance candidate genes (Rpp4C1-05) from PI459025B and three closely related genes from Williams 82 (Rpp4C1-C3). Sequence similarity between these related genes makes it difficult to design an assay which distinguishes between RppC4 from PI459025B and Rpp4C1-C3 from Williams 82. We have identified a region of the sequence from supplemental figure 4 (Meyer et al. Plant Phys 150, 295-307), bp 834-991, containing 11 SNPs, Region 1 (SEQ ID NO. 1) which can be used to distinguish PI459025B Rpp4C4 from Rpp4C1-C3 from ASR susceptible lines such as Williams 82.

TABLE 2

| SNP Number and Positions in Region 1 (SEQ ID NO. 1) | | | | | | | | | | | |
|---|---|---|---|---|---|---|---|---|---|---|---|
| Region 1 SNP Number | 1 | 2 | 3 | 4 | 5 | 6 | 7 | 8 | 9 | 10 | 11 |
| Position of SNP in SEQ ID NO. 1 | 1 | 14 | 36 | 44 | 45 | 51 | 59 | 121 | 143 | 148 | 157 |
| Favorable Allele | C | G | A | G | A | T | G | A | C | G | A |
| Un-favorable Allele | T | A | C | A | T | C | A | T | G | A | T |

SNPs 1, 2, 6, 7, 9, 10 and 11 can be used to distinguish PI45902513 Rpp4C4 from Rpp4C1-C3 from ASR susceptible lines such as Williams 82. A first primer which hybridizes to SNP 1 and 2, a probe which hybridizes to SNP 6 and 7, and a second primer which hybridizes to SNPs 9, 10 and 11 can be used to distinguish PI459025B Rpp4C4 from Rpp4C1-C3 from ASR susceptible lines such as Williams 82. SNPs 1, 2, 6, 7, 9, 10 and 11 correspond to SEQ ID NO. 1 nucleotides 1, 14, 51, 59, 143, 148, and 157. The PCR primers and probes can be used in a TAQMAN, real time PCR, genotyping assay. A second region of the sequence from supplemental figure 4 (Meyer et al. Plant Phys 150, 295-307), bp 286-754 was used to design assays to Rpp4C4. No assays designed to region 2 (SEQ ID NO 2) was optimal for distinguishing PI459025 Rpp4C4 from Williams 82 Rpp4C1-C3 (Table 7).

In some embodiments, as described herein, a combination of SNPs can be used to detect the presence of an Rpp4 resistance allele.

In further embodiments, a marker of this invention can include any marker linked to the aforementioned markers. Linked markers may be determined, for example, by using resources available on the SoyBase internet resource (soybase.org).

The presently disclosed subject matter thus also relates to methods for identifying, selecting, and/or producing soybean plants having an Rpp4 resistance allele comprising detecting in a donor soybean plant the presence of a genetic marker associated with an Rpp4 resistance allele and/or a genetic marker associated with Asian Soybean Rust resistance as described herein and transferring the nucleotide sequence comprising the at least one genetic marker thus detected from the donor soybean plant to a Asian Soybean Rust—recipient soybean plant. It is noted that the recipient soybean plant can be resistant to certain Asian Soybean Rust races and susceptible to other Asian Soybean Rust races. Typically, the recipient soybean plant is at least susceptible to the race of Asian Soybean Rust for which the transfer of the nucleotide sequence comprising the genetic marker (associated with an Rpp4 resistance allele) confers resistance (transferred from the donor soybean plant). In other embodiments, the recipient soybean plant can susceptible to all Asian Soybean Rust races. This allows the breeder to develop soybean plants having resistance to one or more races of Asian Soybean Rust. The transfer of the nucleotide sequence can be performed by any of the methods described herein.

Thus, methods for identifying, selecting and/or producing a soybean plant or germplasm comprising an Rpp4 resistance allele can comprise detecting the presence of a genetic marker associated with an Rpp4 resistance allele. The SNP marker can be detected in any sample taken from the soybean plant or germplasm, including, but not limited to, the whole plant or germplasm, a portion of said plant or germplasm (e.g., a cell, leaf, seed, etc, from said plant or germplasm) or a nucleotide sequence from said plant or germplasm.

Accordingly, in one aspect of the present invention, a method of identifying and/or selecting a soybean plant or germplasm having an Rpp4 resistance allele is provided, the method comprising: detecting, in a soybean plant or germplasm, the presence of a genetic marker associated with an Rpp4 resistance allele, wherein said marker comprises, consists essentially of, a G at nucleotide 59 of SEQ ID NO:1 (SY3131), thereby identifying and/or selecting a soybean plant or germplasm having an Rpp4 resistance allele.

In a further aspect, a method is provided for identifying and/or selecting a Asian Soybean Rust-resistant soybean plant or germplasm, the method comprising: detecting, in a soybean plant or germplasm, the presence of a genetic marker associated with an Rpp4 allele conferring resistance to Asian Soybean Rust, wherein the genetic marker comprises, consists essentially of, or consists of is a G at nucleotide 59 of SEQ ID NO:1 (SY3131), thereby identifying and/or selecting an Asian Soybean Rust-resistant soybean plant or germplasm.

Methods for identifying and/or selecting a soybean plant or germplasm comprising an Rpp4 resistance allele and methods for identifying and/or selecting an Asian Soybean Rust-resistant soybean plant or germplasm can comprise detecting the presence of a marker associated with an Rpp4 resistance allele as described herein.

In other aspects, the present invention provides a method of identifying and/or selecting a Asian Soybean Rust-susceptible soybean plant or germplasm, the method comprising: detecting, in said soybean plant or germplasm, the presence of a genetic marker associated with an Rpp4 susceptible allele, wherein said genetic marker comprises, consists essentially of, or consists of: a G at nucleotide 59 of SEQ ID NO:1 (SY3131), thereby identifying and/or selecting an Asian Soybean Rust-susceptible soybean plant or germplasm. Thus, for example, by identifying plants having these particular genetic markers these plants can be removed from the breeding population.

Exemplary Assay Primers for Genotyping and/or Amplification

As discussed herein, in some embodiments of this invention, a marker can be identified using amplification products generated by amplifying a *Glycine* sp. nucleic acid with two oligonucleotide primers. In some embodiments, the amplification is by PCR, and the primers are PCR primers that are designed to hybridize to opposite strands of the *Glycine* sp. genomic DNA (e.g., Chromosome 18) in order to amplify a *Glycine* sp. genomic DNA sequence present between the sequences to which the PCR primers hybridize in the *Glycine* sp. genomic DNA. Methods of amplifying nucleic acids are well known in the art.

Accordingly, in some embodiments of the present invention, a method of identifying and/or selecting a soybean plant or germplasm having an Rpp4 resistance allele is provided, the method comprising: detecting, in said soybean plant or germplasm, the presence of a genetic marker associated with the Rpp4 resistance allele, wherein said marker is detected in amplification products from a nucleic acid sample isolated from said soybean plant or germplasm using a probe, said amplification products having been produced using pairs of amplification primers wherein said amplification primers and probes have the nucleotide sequences of: SEQ ID NO: 3-4 and SEQ ID NO: 4-5, respectively for SY3131, thereby identifying and/or selecting a soybean plant or germplasm having an Rpp4 resistance allele.

In other embodiments, a method of producing a soybean plant or germplasm having an Rpp4 resistance allele is provided, the method comprising: (a) detecting, in said soybean plant or germplasm, the presence of a genetic marker associated with the Rpp4 resistance allele, wherein said marker is detected in amplification products from a nucleic acid sample isolated from said soybean plant or germplasm using a probe, said amplification products having been produced using pairs of amplification primers, wherein said amplification primers and probes have the nucleotide sequences of: SEQ ID NO: 3-4 and SEQ ID NO: 5-6, thereby identifying and/or selecting a soybean plant or germplasm having an Rpp4 resistance allele. As the skilled artisan would readily recognize, when combinations of SNPs are detected, then combinations of primers and probes are used.

Marker-Assisted Selection

The subject matter disclosed herein also relates to methods for producing pathogen-resistant soybean plants comprising detecting the presence of a genetic marker associated with pathogen resistance in a donor soybean plant according to the methods as described herein and transferring a nucleic acid sequence comprising at least one genetic marker thus detected from the donor plant to a recipient soybean plant. The transfer of the nucleic acid sequence can be performed by any method known in the art.

Thus, the present invention encompasses methods of plant breeding and methods of selecting/identifying plants, in particular soybean plants, particularly cultivated soybean plants as breeder plants for use in breeding programs or cultivated soybean plants having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus *Glycine* having Asian Soybean Rust resistance comprising detecting in the plant the presence of one or more Rpp4 resistance alleles as defined herein. In an exemplary embodiment of the presently disclosed methods for selecting such a plant, the method comprises providing a sample of genomic DNA from a soybean plant; and (b) detecting in the sample of genomic DNA at least one genetic marker associated with Asian Soybean Rust resistance. In some embodiments, the detecting comprises detecting one or more SNPs that are associated with Asian Soybean Rust resistance.

The providing of a sample of genomic DNA from a soybean plant can be performed by standard DNA isolation methods well known in the art.

The detecting of a genetic marker (e.g., SNP, combination of SNPs) can in some embodiments comprise the use of one or more sets of primer pairs (SNP assays) that can be used to produce one or more amplification products that can be used in the detection of genetic markers (SNPs). Such a set of primers can comprise, in some embodiments, nucleotide sequences as set forth in SEQ ID NO: 3-4.

In some embodiments, the detecting of a genetic marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker. In some embodiments, the detecting of a genetic marker is designed to determine whether a particular allele of a SNP is present or absent in a particular plant.

The presently disclosed subject matter thus also relates to methods for producing pathogen-resistant soybean plants comprising detecting the presence of a genetic marker associated with an Rpp4 resistance allele (or a genetic marker associated with Asian Soybean Rust resistance) in a donor soybean plant according to the presently disclosed subject matter as described herein and transferring a nucleotide sequence comprising at least one genetic marker thus detected, or a Asian Soybean Rust resistance-conferring part thereof, from the donor plant to a recipient soybean plant. In particular embodiments, the recipient soybean plant is susceptible to the race of Asian Soybean Rust for which said transferred nucleotide sequence confers resistance. The transfer of the nucleic acid sequence can be performed by any of the methods described herein.

An exemplary embodiment of such a method comprises the transfer of the nucleic acid sequence from a pathogen-resistant donor soybean plant into a recipient soybean plant by crossing the plants by introgression. This transfer can be accomplished by using traditional breeding techniques. Pathogen-resistance loci are introgressed in some embodiments into commercial soybean varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode for the desired trait. As disclosed herein, such identification and selection is based on selection of SNP alleles of this invention or markers associated therewith. MAB can also be used to develop near-isogenic lines (NIL) comprising one or more pathogen resistant alleles of interest, allowing a more detailed study of an effect of such allele(s). MAB is also an effective method for development of backcross inbred line (BIL) populations. Soybean plants developed according to these embodiments can in some embodiments derive a majority of their traits from the recipient plant, and derive pathogen resistance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with pathogen resistance into a recipient soybean plant. The recipient soybean plant may be resistant or susceptible to one or more pathogens or to one or more Asian Soybean Rust races. In some embodiments of the present invention, the recipient soybean plant is susceptible to the Asian Soybean Rust race for which resistance is conferred by transferring said nucleic acid sequence associated with pathogen resistance. Thus, for example, inbred pathogen-resistant soybean plant lines can be developed using the techniques of recurrent selection and backcrossing, selfing, and/or dihaploids, or any other technique used to make parental lines. In a method of recurrent selection and backcrossing, pathogen resistance can be introgressed into a target recipient plant (the recurrent parent) by crossing the recurrent parent with a first donor plant, which differs from the recurrent parent (i.e., non-recurrent parent). The recurrent parent is a plant that is non-resistant or has a low level of resistance to one or more pathogens or to a particular race of a pathogen but, in some embodiments, possesses commercially desirable characteristics, such as, but not limited to (additional) disease and/or insect resistance, valuable nutritional characteristics, valuable abiotic stress tolerance (including, but not limited to, drought tolerance, salt tolerance), and the like. In some embodiments, the non-recurrent parent exhibits pathogen resistance and comprises a nucleic acid sequence that is associated with pathogen resistance (e.g., resistance to Asian Soybean Rust). The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding, for example, Asian Soybean Rust resistance or a genetic marker associated with Asian Soybean Rust resistance (e.g., SNPs and SNP combinations described herein). Also, MAB can be used to confirm the results obtained from the quantitative bioassays. In some embodiments, the markers defined herein are suitable to select proper offspring plants by genotypic screening.

Following screening, F1 hybrid plants that exhibit a pathogen-resistant phenotype or, in some embodiments, the genotype, and thus comprise the requisite nucleic acid sequence associated with pathogen resistance, are then selected and backcrossed to the recurrent parent in order to allow for the soybean plant to become increasingly inbred. The process of selecting and backcrossing can be repeated for a number of generations (e.g., for one, two, three, four, five, six, seven, eight, or more generations).

Thus, a marker that demonstrates linkage with a locus affecting a desired phenotypic trait provides a useful tool for selection of the trait in a plant population. This is particularly true where the phenotype is difficult to assay or occurs at a late stage in plant development. Since marker assays are less laborious and take up less physical space than field phenotyping, much larger populations can be assayed, increasing the chances of finding a recombinant plant with the target segment from the donor line that is moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker." For example, SY3131 is designed to the gene Rpp4C4, a candidate gene for Rpp4 (Meyer et al. Plant Phys 150, 295-307).

The availability of integrated linkage maps of the soybean genome containing increasing densities of public soybean markers has facilitated soybean genetic mapping and MAS. See, e.g. soybeanbreederstoolbox.org, which can be found on the SoyBase internet resource (soybase.org).

Of the types genetic marker available, SNPs are some of the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.), KASPar (LGC Genomics KBioscience, Teddington, Middlesex, UK) and Beadarrays™ (Illumina, San Diego, Calif.).

Accordingly, the genetic markers of the present invention can be used in marker-assisted selection methods to identify and/or select and/or produce progeny having an Rpp4 resistance allele. Such methods can include crossing a first soybean plant or germplasm with a second soybean plant or germplasm, wherein the first soybean plant or germplasm comprises a SNP marker associated with an Rpp4 resistance allele, and selecting a progeny plant that possesses the SNP marker. Therefore, in one embodiment of the present invention, a method of producing a soybean plant having an Rpp4 resistance allele is provided, the method comprising: (a) detecting, in a soybean germplasm, the presence of a genetic marker (SNPs or SNP combinations) associated with an Rpp4 resistance allele, wherein said marker comprises, consists essentially of, or consists of: is a G at nucleotide 59 of SEQ ID NO:1 (SY3131); and (b) producing a soybean plant from said soybean germplasm, thereby producing a soybean plant having the Rpp4 resistance allele.

In other embodiments, the present invention provides a method of introgressing an Rpp4 resistance allele into a soybean germplasm that is lacking the Rpp4 resistance allele, the method comprising: (a) crossing a donor parental soybean line comprising a genetic marker associated with an Rpp4 resistance allele with a recurrent parental soybean line that lacks said marker to produce progeny; (b) selecting progeny comprising said marker and backcrossing said progeny with the recurrent parental soybean line, wherein said progeny are selected by detecting, in their genomes, the presence of the marker associated with an Rpp4 resistance allele, wherein the marker comprises: is a G at nucleotide 59 of SEQ ID NO:1 (SY3131); (c) backcrossing the selected progeny of (b) with the recurrent parental soybean line to produce further progeny; and (d) repeating steps (b) to (c) one or more times (e.g., one, two, three, four, five, six, seven, eight, nine, ten, or more times), thereby introgressing the Rpp4 resistance allele into the recurrent parental line, and thus introgressing the Rpp4 resistance allele into the soybean germplasm that is lacking the Rpp4 resistance allele.

In some embodiments, a method for introgressing an Rpp4 resistance allele into a soybean germplasm lacking the Rpp4 resistance allele, comprises: (a) crossing a plant identified, selected or produced according to any of the methods described herein with a second soybean plant lacking the Rpp4 resistance allele to produce a segregating population of plants; (b) screening the plants from the segregating population of (a) for the Rpp4 resistance allele by detecting, in the plants from the segregating population, the presence of a genetic marker associated with an Rpp4 resistance allele as described herein; and (c) selecting a plant from (b) in which the genetic marker is detected, thereby introgressing an Rpp4 resistance allele into the soybean germplasm.

In other embodiments of this invention, a method of for producing an inbred soybean plant that is homozygous for an Rpp4 resistance allele is provided, the method comprising: (a) selecting a first donor parental line having an Rpp4 resistance allele by detecting, in the first donor parental line, a genetic marker associated with an Rpp4 resistance allele as described herein; (b) crossing the first donor parental line with a second parental line in hybrid combination to produce a segregating plant population; (c) screening the plants from the segregating population of (b) for the Rpp4 resistance allele by detecting, in the plants from the segregating population, the presence of the genetic marker associated with an Rpp4 resistance allele as described herein; (d) selecting plants from the population of (c) having the genetic marker associated with an Rpp4 resistance allele; and (e) screening the selected plants of (d) to identify an inbred soybean plant that is homozygous for the Rpp4 resistance allele, thereby producing an inbred soybean plant that is homozygous for the Rpp4 resistance allele.

Soybean Plants, Parts Thereof, and Germplasms Having Rpp4 Resistance Alleles

The present invention provides soybean plants and germplasms having an Rpp4 resistance allele and resistance to Asian Soybean Rust. As discussed above, the methods of the present invention can be utilized to identify, produce and/or select a soybean plant or germplasm having an Rpp4 resistance allele. In addition to the methods described above, a soybean plant or germplasm having an Rpp4 resistance allele may be produced by any method whereby a marker associated with an Rpp4 resistance allele is introduced into the soybean plant or germplasm by such methods that include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a soybean plant, or part thereof, having an Rpp4 resistance allele (i.e., Asian Soybean Rust-resistant soybean plant or part thereof), obtainable by the methods of the presently disclosed subject matter, are aspects of the presently disclosed subject matter. In some embodiments, the soybean plant of the present invention has more than one Rpp4 resistance allele as described herein.

The soybean plant, or part thereof, of this invention having an Rpp4 resistance allele can be heterozygous or homozygous for the resistance allele. In some embodiments of this invention, the soybean plant has more than one Rpp4 resistance allele and thus, can be heterozygous at some Rpp4 resistance alleles and homozygous at other Rpp4 resistance alleles.

The soybean plant or germplasm may be the progeny of a cross between a variety of soybean and a second variety of soybean that comprises an Rpp4 resistance allele.

The soybean plant or germplasm may be the progeny of an introgression wherein the recurrent parent is a variety of soybean and the donor comprises an Rpp4 resistance allele.

The soybean plant or germplasm may be the progeny of a cross between a first variety of soybean (e.g., a tester line) and the progeny of a cross between a second variety of soybean (e.g., a recurrent parent) and a variety of soybean that comprises an Rpp4 resistance allele (e.g., a donor).

The soybean plant or germplasm may be the progeny of a cross between a first variety of soybean and the progeny of an introgression wherein the recurrent parent is a second variety of soybean and the donor comprises an Rpp4 resistance allele.

Another aspect of the presently disclosed subject matter relates to a method of producing seeds that can be grown into Asian Soybean Rust-resistant soybean plants. In some embodiments, the method comprises providing a Asian Soybean Rust-resistant soybean plant of this invention, crossing the Asian Soybean Rust-resistant plant with another soybean plant, and collecting seeds resulting from the cross, which when planted, produce Asian Soybean Rust-resistant soybean plants.

Accordingly, the present invention provides improved soybean plants, seeds, and/or tissue cultures produced by the methods described herein. In further embodiments, the present invention provides introgressed *Glycine max* plants and/or germplasm produced by the methods described herein.

Compositions for Analysis of a Soybean Genome

In some embodiments, the presently disclosed subject matter provides methods for analyzing the genomes of soybean plants/germplasms to identify those that include desired markers associated with Asian Soybean Rust resistance. In some embodiments, the methods of analysis comprise amplifying subsequences of the genomes of the soybean plants/germplasms and determining the nucleotides present in one, some, or all positions of the amplified subsequences.

Thus, in some embodiments, the present invention provides compositions comprising one or more amplification primer pairs capable of initiating DNA polymerization by a DNA polymerase on a *Glycine max* nucleic acid template to generate a *Glycine max* marker amplicon. In some embodiments, the *Glycine max* amplicon can be used to identify the *Glycine max* marker comprising a nucleotide sequence of SEQ ID NO. 1. In view of the disclosure of SEQ ID NO. 1 as being linked to pathogen resistance loci, one of ordinary skill in the art would be aware of various techniques that could be employed to analyze the sequences of the corresponding soybean nucleic acids. Representative amplification primer pairs can comprise the nucleotide sequences of a forward primer and corresponding reverse primer as set forth hereinabove in SEQ ID NOs 3 and 4.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

SNP Analysis

There are SSR markers which are associated with soybean rust resistance gene Rpp4. This SSR information was employed to identify SNP markers that map to the regions of qualitative genes and a quantitative trait loci (QTL) region for Rpp4. The identified SNPs were validated on soybean rust resistant and susceptible lines. Analysis indicated that these SNPs mapped more closely and showed better associations to the Rpp gene than did the SSRs. The information of validated SNPs for soybean rust is new and is used for appropriate breeding programs. An ideal marker for a trait such as resistance Asian Soybean Rust would fall within the gene that causes the resistance. The greater the distance between a marker and a causative gene, the more likely that the linkage between the marker and the trait will be broken. A candidate gene, Rpp4C4, has been proposed by Meyer et al. Plant Phys. 150, 295-307. A difficulty for assay design is that the candidate gene exists as a part of a three member gene family in the susceptible line Williams 82 and a five member gene family in the resistant line PI459025B. An assay needs to distinguish between a resistant Rpp4 locus with Rpp4C1, Rpp4C2, Rpp4C3, Rpp4C4, and Rpp4C5 from PI459025B and a susceptible Rpp4 locus with Rpp4C1, Rpp4C2 and Rpp4C3. Many unsuccessful attempts were made to design an assay to the Rpp4C4 gene which failed due to sequence similarities between Rpp4C1, Rpp4C2, Rpp4C3, Rpp4C4, and Rpp4C5. We have identified a combination of seven nucleotides: a C at nucleotide 1 of SEQ ID NO. 1, an G at nucleotide 14 of SEQ ID NO. 1, a T at nucleotide 51 of SEQ ID NO. 1, a G at nucleotide 59 of SEQ ID NO. 1, a C at nucleotide 143 of SEQ ID NO. 1, a G at nucleotide 148 of SEQ ID NO. 1, and an A at nucleotide 157 of SEQ ID NO. 1 interrogated by a single marker assay, SY3131, which distinguishes a soybean plant with a favorable PI459025B allele of Rpp4 for resistance to Asian Soybean rust and an unfavorable allele. A G at nucleotide 59 of SEQ ID NO.1 indicates the resistant Rpp4 locus, however an A at nucleotide 59 of SEQ ID NO.1 can indicate a resistant or susceptible locus depending on assay design because gene family members Rpp4C1 and Rpp4C2 have this sequence variant in both susceptible and resistant lines. It is recognized that a combination of assays could be used to interrogate the SNPs discussed herein.

Example 2

SNP Genotyping

Molecular markers were identified for the Rpp4 gene. Rpp4 was mapped in PI459025 on LG G between SSR Satt288 and AF162283 (Silva et al. 2008, Theor Appl Genet 117:57-63). The approximate positions of these genes and the various markers are depicted in Table 3.

TABLE 3

| Marker | AF162283 | SY3131 | Satt 288 |
|---|---|---|---|
| Linkage Group | G | G | G |
| Genetic Position | 79.793 cM | 76.0 cM | 71.577 cM |
| Chromosome | Gm18 | Gm18 | Gm18 |

The soybean linkage map developed by scientists at the USDA and made publicly available in 2006 can be found through the website of the United States Department of Agriculture (USDA) and is discussed in Choi et al. (2007) Genetics 176:685-696. This map was used to locate the flanking SSRs that were mapped within and close to each region. The Soybean genome project initiated by the U.S. Department of Energy Joint Genome Institute published an 8× genome assembly Schmutz et al. Nature 463, 178-183. The genome assembly is available on the World Wide Web through the Joint Genome Institute "Phytosome" database or the United States Department of Agriculture (USDA) "Soy-Base" database.

The polymormphism information and genomic sequence on either side of the SNP was used to design PCR-based assays to detect each allele. The sequences with the SNP indicated were either submitted to the Applied Biosystems Inc. (ABI; Foster City, Calif., United States of America) Assays-by-Design service for creation of custom TAQMAN R (Applied Biosystems Inc., Foster City, Calif., United States of America) based assays, or assays were manually designed using the ABI software Primer Express R. Similarly, Taqman R assays can be designed using software available from Biosearch Technologies (Novato, Calf., United States of America). A goal of the SNP assay was to be able to determine which polymorphism(s), or allele(s), is/are present in the genome of any given soybean line, and ultimately to permit the selection of preferred allele(s)(i.e., rust resistant gene(s), in a marker-assisted breeding program. DNA isolated from the resistant line PI459025B was used for the assays.

| Assay id | Assay component name | SEQ ID NO. | Allele Distinguished | Fluo color | Allele/ Detected nucleotide |
|---|---|---|---|---|---|
| SY3131 | SY3131F1 | 3 | Favorable | | |
| SY3131 | SY3131R1 | 4 | Favorable | | |
| SY3131 | SY3131A1FM | 5 | Favorable | FM | G |
| SY3131 | SY3131A2TT | 6 | Unfavorable | TT | A |
| SY2757 | SY2757F1 | 7 | | | |
| SY2757 | SY2757R1 | 8 | | | |
| SY2757 | SY2757A1FM | 9 | Favorable | FM | G |
| SY2757 | SY2757A2TT | 10 | Unfavorable | TT | A |
| SY2758 | SY2758F1 | 11 | | | |
| SY2758 | SY2758R1 | 12 | | | |
| SY2758 | SY2758A1FM | 13 | Favorable | FM | A |
| SY2758 | SY2758A2TT | 14 | Unfavorable | TT | T |
| SY2759 | SY2759F1 | 15 | | | |
| SY2759 | SY2759R1 | 16 | | | |
| SY2759 | SY2759A1FM | 17 | Favorable | FM | G |
| SY2759 | SY2759A2TT | 18 | Unfavorable | TT | C |
| SY2760 | SY2760F1 | 19 | | | |
| SY2760 | SY2760R1 | 20 | | | |
| SY2760 | SY2760A1FM | 21 | Favorable | FM | A |
| SY2760 | SY2760A2TT | 22 | Unfavorable | TT | G |
| SY2960 | SY2960F1 | 23 | | | |
| SY2960 | SY2960R1 | 24 | | | |
| SY2960 | SY2960A1FM | 25 | Favorable | FM | G |
| SY2960 | SY2960A2TT | 26 | Unfavorable | TT | A |
| SY2961 | SY2961F1 | 27 | | | |
| SY2961 | SY2961R1 | 28 | | | |

-continued

| Assay id | Assay component name | SEQ ID NO. | Allele Distinguished | Fluo color | Allele/ Detected nucleotide |
|---|---|---|---|---|---|
| SY2961 | SY2961A1FM | 29 | Favorable | FM | A |
| SY2961 | SY2961A2TT | 30 | Unfavorable | TT | T |
| SY2962 | SY2962F1 | 31 | | | |
| SY2962 | SY2962R1 | 32 | | | |
| SY2962 | SY2962A1FM | 33 | Favorable | FM | G |
| SY2962 | SY2962A2TT | 34 | Unfavorable | TT | A |
| SY2963 | SY2963F1 | 35 | | | |
| SY2963 | SY2963R1 | 36 | | | |
| SY2963 | SY2963A1FM | 37 | Favorable | FM | G |
| SY2963 | SY2963A2TT | 38 | Unfavorable | TT | T |
| SY2964 | SY2964F1 | 39 | | | |
| SY2964 | SY2964R1 | 40 | | | |
| SY2964 | SY2964A1FM | 41 | Favorable | FM | C |
| SY2964 | SY2964A2TT | 42 | Unfavorable | TT | G |
| SY2965 | SY2965F1 | 43 | | | |
| SY2965 | SY2965R1 | 44 | | | |
| SY2965 | SY2965A1FM | 45 | Favorable | FM | A |
| SY2965 | SY2965A2TT | 46 | Unfavorable | TT | G |
| SY2966 | SY2966F1 | 47 | | | |
| SY2966 | SY2966R1 | 48 | | | |
| SY2966 | SY2966A1FM | 49 | Favorable | FM | C |
| SY2966 | SY2966A2TT | 50 | Unfavorable | TT | A |
| SY2967 | SY2967F1 | 51 | | | |
| SY2967 | SY2967R1 | 52 | | | |
| SY2967 | SY2967A1FM | 53 | Favorable | FM | A |
| SY2967 | SY2967A2TT | 54 | Unfavorable | TT | G |
| SY2968 | SY2968F1 | 55 | | | |
| SY2968 | SY2968R1 | 56 | | | |
| SY2968 | SY2968A1FM | 57 | Favorable | FM | A |
| SY2968 | SY2968A2TT | 58 | Unfavorable | TT | G |
| SY2969 | SY2969F1 | 59 | | | |
| SY2969 | SY2969R1 | 60 | | | |
| SY2969 | SY2969A1FM | 61 | Favorable | FM | T |
| SY2969 | SY2969A2TT | 62 | Unfavorable | TT | A |
| SY2970 | SY2970F1 | 63 | | | |
| SY2970 | SY2970R1 | 64 | | | |
| SY2970 | SY2970A1FM | 65 | Favorable | FM | G |
| SY2970 | SY2970A2TT | 66 | Unfavorable | TT | T |

DNA can be extracted from plant tissue in any way known in the art, including the CTAB (hexadecyltrimethylammonium bromide) method (See, e.g., Stewart et al., *BioTechniques* 14(5):748-749 (1993)), sodium hydroxide, and the Dellaporta method (Dellaporta et al., Plant Mol. Biol. Rep. 1:19-21 (1983)). See also, Sambrook & Russell *Molecular Cloning: A Laboratory Manual, Third Edition*, Cold Spring Harbor Laboratory Press, Cold Spring Harbor, N.Y., United States of America (2001)) for additional DNA extraction methods. DNA is diluted in TE buffer and stored at 4° C. until used in PCR reactions as described below in Table 5.

TABLE 5

PCR was set up in 5 µl final volumes according to the following formula.

| Reagent | Stock concentration | Per reaction (µl) | For 96 samples (µl) | Final concentration |
|---|---|---|---|---|
| 2X Master Mix (JumpStart ™ Taq ReadyMix ™) | 2X | 2.5 | 296.88 | 1X |
| AbD primer/probe mix (80x) | 40x | .0625 | 6 | 0.5x |
| PCR-quality H2O | — | 2.44 | 234.24 | — |
| DNA (dried in 384) | 4.5 ng/µl | 4 | — | 3.6 ng/ul (18 ng) |
| Final Volume (ul) | | 5.00 | 357.44 | |

The Master Mix is JumpStart™ Taq ReadyMix™ (Sigma Catalogue No. 2893; Sigma Chemical Co., St. Louis, Mo., United States of America), a premix of all the components, including nucleotides and Taq polymerase (but not primers and/or probes) necessary to perform a 5'-nuclease assay. Before use, 1375 µl of 1.0 M $MgCl_2$ (Sigma Catalogue No. M1028) and 250 µl of 300 µM Sulforhodamine 101 (Sigma Catalogue No. S7635), also known as ROX, are added to a 125 mL bottle of JumpStart™ Taq ReadyMix™. PCR plates were placed in an ABI 9700 thermal cycler and the program set forth in Table 10 was run:

TABLE 6

PCR program.

| Task | SNP1 |
|---|---|
| Initial denaturation | 50° C. for 2 min; followed by 95° C. for 10 min |
| Cycles | 95° C. for 15 sec |
| | 60° C. for 1 min |
| Number of cycles | 40 |
| Final elongation | 72° C. for 5 min |
| Hold | Hold at 4° C. |

The ABI 7900 Sequence Detection System (or Taqman®) was used to visualize the results of an allelic discrimination (SNP) assay. Using the Sequence Detection System (SDS) software, allele calls were made based on the fluorescence for the two dyes measured in each sample.

As shown in Table 7, all assays designed to region 2 failed to perform. Assays designed to region 1 had mixed performance. Assays SY2757, SY2758 and SY2759 failed to perform. Assay SY2760 had non-optimal performance as it gave an ambiguous signal for ASR resistant samples. Only SY3131 had optimal performance correctly and clearly identifying ARS sensitive and Rpp4 lines as shown in Table 8.

TABLE 7

| SY2757 | Region 1 | Failed |
|---|---|---|
| SY2758 | Region 1 | Failed |
| SY2759 | Region 1 | Failed |
| SY2760 | Region 1 | Non-optimal |
| SY3131 | Region 1 | Optimal |
| SY2960 | Region 2 | Failed |
| SY2961 | Region 2 | Failed |
| SY2962 | Region 2 | Failed |
| SY2963 | Region 2 | Failed |
| SY2964 | Region 2 | Failed |
| SY2965 | Region 2 | Failed |
| SY2966 | Region 2 | Failed |
| SY2967 | Region 2 | Failed |
| SY2960 | Region 2 | Failed |
| SY2961 | Region 2 | Failed |
| SY2962 | Region 2 | Failed |

TABLE 8

| Soybean Line | | Genotype SY3131 |
|---|---|---|
| PI 459025 B | Rpp4 | G |
| Wayne | susceptible | A |
| Centennial | susceptible | A |
| Dwight | susceptible | A |
| Loda | susceptible | A |
| BENNING | susceptible | A |
| DAVIS | susceptible | A |
| FORREST | susceptible | A |
| ESSEX | susceptible | A |

TABLE 8-continued

| Soybean Line | | Genotype SY3131 |
|---|---|---|
| Jack | susceptible | A |
| Dillon | susceptible | A |
| WILLIAMS 82 | susceptible | A |

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of producing a soybean plant having an Asian soybean rust (ASR) resistance, the method comprising the steps of:

a) isolating a nucleic acid from a soybean plant cell;

b) detecting in the nucleic acid of a) the presence of a haplotype associated with an ASR resistance allele, wherein said haplotype comprises a C at nucleotide 1 of SEQ ID NO: 1, a G at nucleotide 14 of SEQ ID NO: 1, a T at nucleotide 51 of SEQ ID NO: 1, a G at nucleotide 59 of SEQ ID NO: 1, a C at nucleotide 143 of SEQ ID NO: 1, a G at nucleotide 148 of SEQ ID NO: 1, and an A at nucleotide 157 of SEQ ID NO: 1;

c) identifying a first soybean plant on the basis of the presence of the haplotype detected in b);

d) crossing the first soybean plant with a second soybean plant not comprising said haplotype; and e) producing a progeny plant from the cross of d), wherein said progeny plant comprises the haplotype detected in b), thereby producing a soybean plant having ASR resistance.

* * * * *